United States Patent [19]

Korpman

[11] 4,314,558
[45] Feb. 9, 1982

[54] SURGICAL DRAINAGE BAGS

[75] Inventor: Ralf Korpman, Bridgewater, N.J.

[73] Assignee: Permacel, New Brunswick, N.J.

[21] Appl. No.: 144,497

[22] Filed: Apr. 28, 1980

[51] Int. Cl.³ .............................................. A61F 5/44
[52] U.S. Cl. .................................. 128/283; 128/295;
128/760; 128/DIG. 24; 150/3; 206/265;
215/200; 229/62
[58] Field of Search ............... 128/292, 760, 767, 272,
128/275, 283, 295, DIG. 24; 150/3, 7; 206/265;
215/200, 232; 229/62

[56] References Cited

U.S. PATENT DOCUMENTS

| | | | |
|---|---|---|---|
| 2,703,576 | 3/1955 | Furr, Jr. | 128/283 |
| 3,344,789 | 10/1967 | Arnold et al. | 128/295 |
| 3,612,053 | 10/1971 | Pratt | 128/283 |
| 3,669,103 | 6/1972 | Harper et al. | |
| 3,683,918 | 8/1972 | Pizzella | 128/283 |
| 3,690,320 | 9/1972 | Riely | 128/283 |
| 3,759,260 | 9/1973 | Nolan et al. | 128/283 |
| 3,797,734 | 3/1974 | Fleury et al. | 229/62.5 |
| 3,810,468 | 5/1974 | Harper et al. | |
| 4,166,706 | 9/1979 | Korpman | |
| 4,197,849 | 4/1980 | Bostick | 128/295 |

Primary Examiner—C. Fred Rosenbaum
Attorney, Agent, or Firm—Alice O. Robertson

[57] ABSTRACT

The invention describes surgical drainage bags suitable for receiving body fluids and wastes. One aspect of the invention is a self-sealing bag of flexible film in which the opening may be sealed by stretching, relaxing and pressing the sides of the opening together. Another aspect of the invention is the incorporation of an absorbent product into surgical bags. The preferred embodiment embraces both these aspects. Suitable materials for the bag and the absorbent products are described.

6 Claims, 9 Drawing Figures

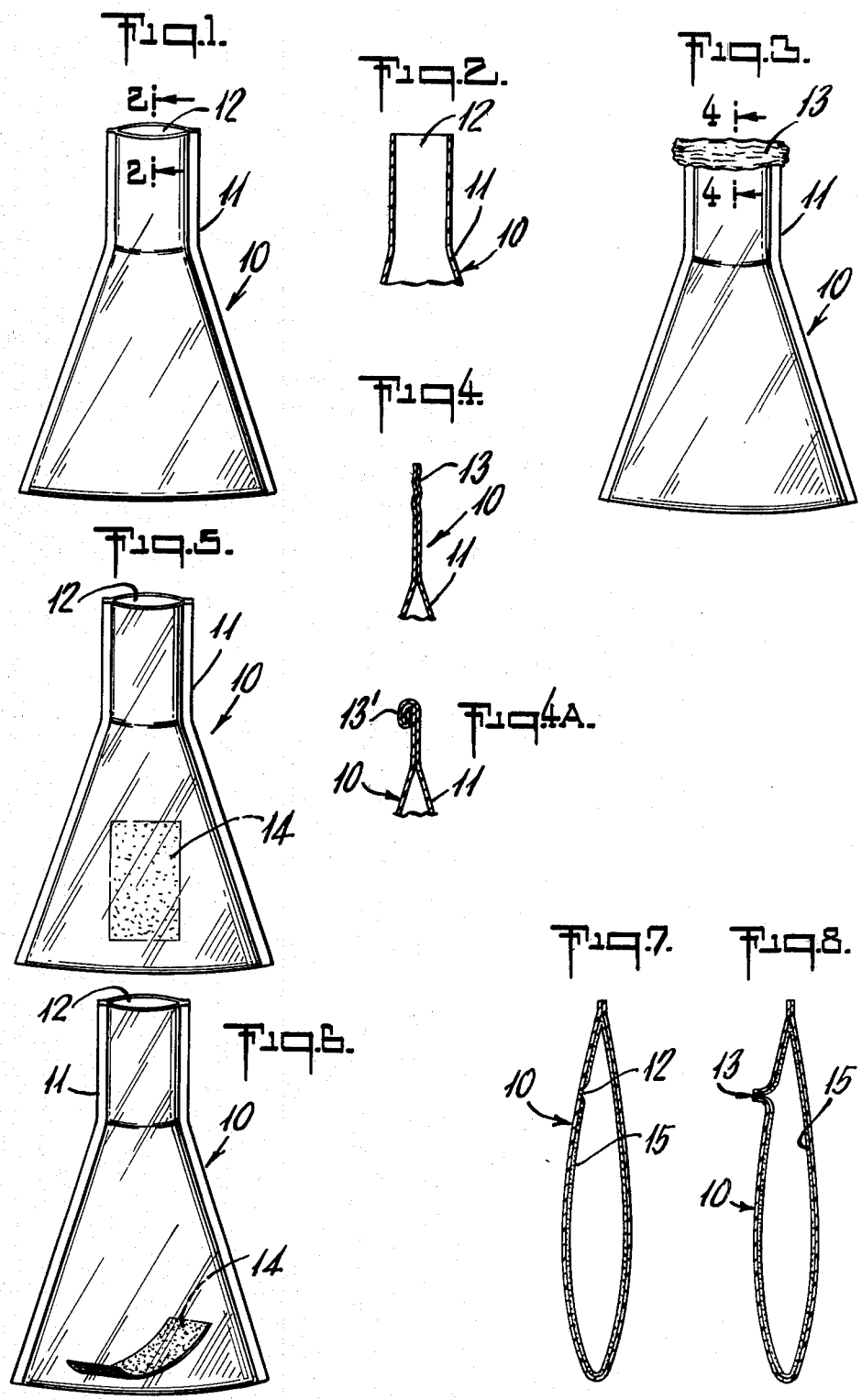

SURGICAL DRAINAGE BAGS

This invention relates generally to receptacles or bags, and more particularly to receptacles suitable for use after colostomies, ileostomies, urostomies, ureterostomies and the like.

Surgery often results in the creation of an orifice or stoma through which drainage of body fluids and/or waste materials must be accomplished. Collection and disposal of such body fluids and waste materials are generally carried out in flexible bags which are attached around the stoma by means of an adhesive or by straps fastened around the body, or by attachment devices. U.S. Pat. Nos. 3,736,934, 3,869,762, and 4,137,918 describe some of the devices or means by which bags may be attached to the stoma. Generally, the bags are of flexible plastic materials. At the time of disposal, the bag is taken from the attachment and the contents flushed immediately or the opening is closed by the tying or fastening for ultimate disposal. Not infrequently manipulating a fluid-filled flexible bag is an awkward and unpleasant procedure.

The present invention avoids the foregoing problems by the provision of two improvements which may be separately employed but which is most advantageously employed together. One aspect of the present invention is the provision of a self-sealing, flexible, fluid-impervious, disposable receptacle or bag in which the opening may be closed without a supplemental aid such as wire, or string or tape, and in which the closure can be accomplished readily either prior to or subsequent to removal from the point of attachment to the body. By use of a particular flexible thermoplastic-elastomeric film for the receptacle or bag, the bag may be closed and sealed merely by stretching, relaxing, and pressing together the walls of the bag adjacent to the opening with or without folding as hereinafter more fully described. The self-sealing nature of the bag of the present invention avoids the need for supplemental aids thereby facilitating the manipulations during disposal.

The flexible, normally non-tacky non-elastic film to be employed for the bag is made from a blend of (a) a thermoplastic-elastomeric block copolymer component and (b) a resin component, wherein the resin is one which tends to associate with the thermoplastic block of the block copolymer as hereinafter more fully detailed. The film is characterized by having the property of undergoing visible deformation or transformation on the application of a substantial stretching force. The deformation is accompanied by a change in the property of the film from a non-tacky, plastic, inelastic character to a somewhat tacky, elastic character. The change is retained for a long period on relaxation or removal of the stretching force. The force to be applied is that sufficient to stretch the film at least 100 percent, preferably several hundred percent. By "stretching" or "stretching and relaxing" as hereinafter employed is meant to embrace the application of sufficient force to cause the transformation to take place and the removal of the force after the transformation.

Another aspect of the present invention and a preferred embodiment when employing the above-described bag is the incorporation of an absorbent in the interior of the bag providing for immobilization of fluid. The absorbent may be in a free particulate state but also may be a product of particulate borne on a matrix, said matrix preferably in the form of a film. The absorbent film may be a lining, a piece attached to the inner wall, or an unattached insert. The presence of the absorbent removes flowable fluid facilitating handling procedures and also avoids fluid flow should a leakage develop in the receptacle. The use of absorbent film is particularly advantageous over use of free particulate absorbents which are generally powders and which may become lost through spillage prior to use. The absorbent film piece or lining is readily incorporated during manufacture.

The most preferred embodiment of the present invention contemplates the inclusion of the absorbent as an absorbent film in a bag thereby providing a flexible, fluid-impervious, fluid-immobilized disposable surgical receptacle or bag.

The drawings illustrate preferred embodiments of the present invention and illustrate features and advantages of the invention but are not to be construed as a limitation on the scope thereof. In the drawing:

FIG. 1 is a view of one form of the surgical drainage bag showing an opening which is to be attached to the stoma by means of an adhesive or any suitable attachment device.

FIG. 2 is an enlarged sectional view along 2—2 FIG. 1 showing the opening of the bag.

FIG. 3 is a view showing the sealed opening of the bag after having been stretched, relaxed and pressed together.

FIG. 4 is an enlarged sectional view along line 4—4 of FIG. 3 showing the sides of the opening sealed together.

FIG. 4a shows sides of the opening folded over before being sealed.

FIG. 5 is a view of the bag showing a piece of absorbent film attached to a portion of the inner wall.

FIG. 6 is a view showing a piece of absorbent film included in the bag as an unattached insert.

FIG. 7 is a sectional view of a flat bag in which an absorbent film lines the bag and also in which the opening is positioned on one side.

FIG. 8 is a view of FIG. 7 after closure.

Referring to the drawings, FIG. 1 shows a surgical drainage bag 10 comprising a wall 11 with an opening 12 suitable for attachment to a stoma employing disposable adhesion means or reusable attaching device and through which body fluids and waste materials enter the bag for collection. Any known suitable attachment means may be employed. When the collection has been completed, the bag is stretched at or near the opening, relaxed and pressed together as seen in FIG. 3 to form a seal 13, enclosing the fluid and waste materials in the bag. The nature of the closure is seen by comparing FIGS. 2 and 4. The stretched opening may be folded prior to pressing together to form seal 13' as seen in FIG. 4a.

Although the bag is illustrated primarily as one having a broad base with a neck and an opening at the neck, the bag may be of any shape. Further, the opening may be variously positioned and also of any shape although preferably, it is narrow or slitted.

The provision of a surgical receptacle, sealable without adhesive or separate device is predicated on the use of a particular material. The material to be employed for the receptacle or bag of this invention is a film having both thermoplastic and elastic properties and made from a composition consisting of a blend of (a) an elastomer component comprising thermoplastic-elastomeric block copolymers wherein the thermoplastic blocks are derived from alkenylarenes and the elastomeric blocks are derived from conjugated dienes or lower alkenes and (b) a plastic component comprising resins which tend to associate principally with the thermoplastic alkenylarene blocks of the thermoplastic-elastomeric block copolymers. The relative amounts of the thermoplastic-elastomeric block copolymer and thermoplastic block associating resins are important. The amount of thermoplastic block associating resin is from about 30 to about 130 parts, preferably about 60 to about 110 parts by weight for every 100 parts of the thermoplastic-elastomeric block copolymer.

Suitable thermoplastic-elastomeric block copolymers are those of the type conventionally designated in the art as A-B-A block copolymers wherein A designates a thermoplastic block and B designates an elastomeric block. Also included among suitable thermoplastic-elastomeric block copolymers are mixtures of A-B-A and A-B block copolymers. In A-B-A block copolymers all end blocks are thermoplastic while A-B block copolymers have an elastomeric end block as well as a thermoplastic end block. Preferably, the block copolymers are A-B-A block copolymers; if mixtures of A-B-A and A-B block copolymers are employed, the A-B block copolymer is employed in a minor proportion.

In the A-B-A block copolymers, the A-blocks are derived from alkenylarenes, particularly styrene, but also from vinyltoluene, α-methylstyrene, tert-butylstyrene, vinylnaphthalene, vinyltoluene, vinylxylene, 2-vinylpyridine and the like and the B-blocks are derived preferably from conjugated dienes, such as isoprene, butadiene, pentadiene-1,3, 2,3-dimethylbutadiene and the like, but also from lower alkenes such as ethylene and butylene. Representative block polymers are polystyrene-polisoprene-polystyrene (S-I-S) and polystyrene-polybutadiene-polystyrene (S-B-S) block copolymers. Small proportions of other monomers, such as methyl methacrylate also may enter into the block copolymer. The individual A-block have a number average molecular weight of at least about 6,000, preferably in the range of about 8,000 to about 30,000 and constitute about 5 to 50 percent, preferably 10 to 30 percent by weight of the block copolymer. The B-blocks usually have a number average molecular weight of at least about 45,000, preferably in the range of about 45,000 to 180,000. The number average molecular weight of the block copolymer is in the range of about 75,000 to 200,000 for a linear copolymer and in the range of about 125,000 to 400,000 for a radial block copolymer. The designation "A-B-A" as herein employed includes A-B-C block copolymers, i.e., those wherein the endblocks are derived from different alkenylarenes. The term "linear block copolymer" includes branched as well as unbranched copolymers.

The radial A-B-A polymers useful in preparing films for the bags of the invention generally conform to the formula $(A-B)_nX$, wherein A-B is as previously defined and X is an organic or inorganic polyfunctional atom or molecule and in which each (A-B) radiates from X in a way that A is an endblock. X is at least 3 and is frequently 4 or 5 but not limited thereto. Suitable polymers are described in U.S. Pat. No. 3,281,383 and in an article entitled "New Rubber is Backed by Stars" appearing on page 35 of June 11, 1975 issue of *Chemical Week*. Many of the block copolymers are obtainable commercially under trade names such as Kraton 1102 ® (S-B-S) and 1107 ® (S-I-S) (both linear copolymers from Shell Chemical Company), Solprene ® 418 (S-B-S) and 420 (S-I-S) (both radial block copolymers from Phillips Petroleum Company) and Solprene ® 311X and 1205 (both simple A-B block copolymers also from Phillips Petroleum Company).

In the simple A-B block copolymers, the A and B blocks are derived from monomers similar to those of the A-B-A copolymers. Representative copolymers are described in U.S. Pat. Nos. 3,519,585 and 3,787,531. Generally they are in the same molecular weight range as that of the linear A-B-A block copolymers.

The thermoplastic-elastomeric block copolymer component (i.e. elastomer component) of the composition may include small amounts of other more conventional elastomers but if included, these should not exceed about 25 percent by weight of the total elastomers in the composition. These conventional elastomers may include highly broken down natural rubber, synthetic polyisoprene rubber, chloroprene rubber, nitrile rubber, butyl rubber and the like. Elastomeric liquid polymers such as depolymerized rubber, synthetic isoprene and liquid SBR rubber also may be included but if employed they should not exceed above about 10 percent by weight of the total elastomers.

The plastic or resin component of the composition consists essentially of low molecular weight resins which tend to associate or be compatible principally with the thermoplastic A blocks of the block copolymers, and which when mixed with the thermoplastic-elastomeric block copolymers are capable of producing a non-tacky film which exhibits a plastic state at low elongations and an elastomeric state at high elongations, and which is converted from its non-tacky plastic state to a tacky elastomeric state by applying stress. Suitable resins are normally solid and possess a number average molecular weight not above about 3,000, although higher molecular weight resins may be employed if employed in lesser amounts. Preferred A block associating resins include α-methylstyrene-vinyltoluene copolymer and coumarone-indene copolymer. A suitable α-methylstyrene-vinyltoluene copolymer may be obtained as Piccotex 100 and 120 from Hercules Chemical Company. Suitable coumarone-indene copolymer resin may be obtained as Cumar 509 LX resin from Neville Chemical Company. Other A block associating resins include polystyrene and polyindene. Small proportions, i.e., not above about 25 percent of the total resin content, of still other resins also may be included. Although the A block associating resins are normally solid, a small amount of liquid A block associating resin may be present provided that the resulting mixture is solid at room temperatures (70°-80° F.).

The compositions also may contain small proportions of other material such as antioxidants, heat stabilizers, ultraviolet absorbers, extenders, fillers and the like. Typical antioxidants are 2,5-ditertiary-amylhydroquinone and ditertiary-butylcresol. Suitable heat stabilizers include zinc salts of alkyl dithiocarbamates. Relatively small proportions, not above about 25 parts by weight of the total elastomers, of various extenders such as polystyrene, nonreactive phenol-formaldehyde resins, linear polyester resins, polyethylene, polypropylene, and the like also may be included. Additionally, the film forming composition may include relatively small proportions of fillers and pigments such as zinc oxide, aluminum hydrate, clay, calcium carbonate, titanium dioxide, carbon black and the like. The film may be prepared from the components above described by any conventional procedure for preparing films. Conveniently, it is prepared by extrusion, preferably in the temperature range of 325° to 400° F.

Another aspect of the invention is a provision of a flexible fluid drainage bag with an absorbent. This aspect of the invention may be practiced with any surgical drainage receptacle or bag known in the art. Thus, ostomy bags and other surgical drainage receptacles commonly made of polyethylene, vinyl films, elastomers and the like may be provided with an absorbent as hereinafter described in connection with the preferred embodiment.

In a preferred embodiment, the self-sealing bag of the present invention is provided with an absorbent. The absorbent may be provided either as free-flowing powder, or imbedded in or carried on a flexible matrix. When it is provided as a powder, the interior of the bag may be dusted with the absorbent. The absorbent may be any water-insoluble water-swellable absorbent known in the art but is preferably of the kind hereinafter described in connection with the most preferred embodiment.

Preferably the absorbent is provided in a matrix, conveniently as an absorbent bearing film as seen in FIGS. 5–7. Generally when the absorbent is borne on a film, a small piece of absorbent film 14 supplies sufficient absorbent material to remove free liquid. On the other hand, if the bag is made from flat sheets with the edges heat-sealed, it may be more convenient as a method of manufacture to make the bag from a double layer of film with the absorbent layer becoming the inner surface lining 15 of the bag as seen in FIG. 7. In the most preferred embodiment, the absorbent is dispersed on a water-insoluble substantially non-swelling matrix, of an elastomeric-thermoplastic polymer or a thermoplastic polymer as subsequently defined. The absorbent is in the form of particulate matter from 1 micron to $10^4$ micron in diameter and is preferably on a matrix which is in the form of a film but may have any shape achievable by extrusion or solvent casting. The particulate absorbent is present in the range from about 4 to 200 parts for every 100 parts of matrix polymer. The matrix may have a thickness ranging from about 1 mil to about 10 mils. The absorbent so provided is insoluble and substantially swellable in aqueous systems and further is resistant to disintegration when wet. The absorbent which is insoluble in water but swellable and capable of absorbing many times its own weight of water or aqueous fluids including body fluids is selected from organic polymers which may be completely synthetic or may be of modified natural molecules as subsequently more fully described.

In the absorbent materials to be employed, hydrophilic groups constitute at least 25 percent and up to 72 percent of the molecular structure and the polymer network is lightly cross-linked imparting a limited water-insolubility property to the molecules. Suitable water-insoluble materials have a minimum average molecular weight per cross-linkage of about 13,000 and a maximum molecular weight per cross-linkage of about 276,000. These materials are frequently spoken of in the art as "hydrogels" or "hydrocolloid polymers" or "superabsorbents". The preferred polymers have an acrylate group in their molecular structure. They may be completely synthetic acrylate polymers or acrylate modified polysaccharides, e.g., acrylate modified starch or acrylate modified cellulose. "Acrylate polymers" or "polyacrylate" embraces not only polymers of acrylate salts but those in which the hydrophilic group is an acrylamide, acrylic acid or acrylic ester. The absorbents may have another type of hydrophilic group such as sulfonate, oxide, etc. in the structure; such absorbents include sulfonated polystyrene, poly(alkylene oxide), and the like. Carboxymethylcellulose after cross-linking is also within the scope of absorbents. The preferred absorbents are completely synthetic acrylate polymer, acrylate modified starch, acrylate modified cellulose and cross-linked carboxymethylcellulose, embraced within "polyacrylate" herein and are available commercially.

The flexible matrix of the non-disintegrative aqueous fluid absorbent product used in the preferred embodiment of the present invention may be an elastomer preferably a thermoplastic-elastomeric block copolymer similar to those employed in the bag itself but also may be natural rubber, synthetic rubbers such as styrene-butadiene rubber, or it may be of a thermoplastic material such as a copolyester (an ester derived from two different ester units), vinyl polymers, and the like; polypropylene and polyethylene are less desirable because of tendency toward stiffness.

One of the preferred matrixes is that of a thermoplastic-elastomeric block copolymer similar to that employed as the elastic component in the composition from which the film of the bag of the present invention is prepared. Thus, A-B-A and mixtures of A-B block copolymer as previously defined may be employed. Further, for use as matrix material for the absorbent, an A-B block copolymer may be employed in major proportion or even as the sole polymer.

Another preferred matrix is that of a copolyester, i.e., a polymer of at least two identifiable ester units which may be represented by the formulas:

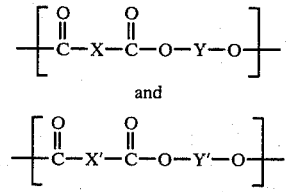

and wherein X and X' are nuclei of dicarboxylic acids and Y and Y' are nuclei of aliphatic diols. The different ester units may arise from the condensation of (a) two different acids with the same diol, (b) two different diols with the same acid, or (c) two different acids and two different diols. The copolyesters may be random, segmented or alternating copolyesters. Generally one ester unit of the copolyester is highly crystalline and one ester unit substantially less crystalline or even noncrystalline. Among the aromatic and aliphatic dicarboxylic acids suitable in the copolyesters are terephthalic acid, isophthalic acid, oxalic acid, maleic acid and the like. Suitable aliphatic diols include ethylene glycol, 1,3-propylene glycol, diethylene glycol, dipropylene glycol and the like. A particularly preferred copolyester is poly-(ethylene terephthalate-co-ethylene azelate) available commercially under the designation VPE 5571 available from Goodyear Tire and Rubber Company. In addition, polymer alloys of copolyester with the block copolymers also provide a suitable matrix.

The absorbent product, namely absorbent borne on a matrix, may be prepared by several methods. When the absorbent is stable to extrusion temperature of the matrix polymer, the product may be prepared by extrusion. Some of the absorbents which are suitable include polyacrylate, sulfonated polystyrene, poly(alkylene oxide) and the like. One convenient method of carrying out the extrusion method is to blend from about 5 to 150 parts, preferably 5 to 75 parts, of absorbent polymer for every 100 parts of matrix polymer and feeding the blended mixture into the extruder. The preblending is preferably carried out a temperature range of from about 225° F. to about 275° F. and the extrusion from about 300° F. to about 450° F.

Alternatively, if the matrix polymer is adaptable to solvent casting as is the thermoplastic elastomeric A-B-A block copolymers, a solvent casting composition may be prepared by mixing absorbent and matrix polymer in a solvent such as toluene or xylene with an antioxidant such as zinc dibutyl dithiocarbamate or 2,5-ditertiary butylhydroquinone and cast onto a suitable surface employing conventional means to obtain an absorbent product in the form of absorbent bearing film.

The absorbent product prepared by any of the conventional methods may be modified to form a discontinuous planar surface. Such surface may be reticulated or may contain embossed patterns of protrusions and depressions. Reticulated films are of special value for superior rate of fluid uptake. Preparation of absorbent products having such modifications may be carried out in accordance with procedures well known in the art.

The absorbent bearing products particularly suitable for incorporating into the bags of the present invention are described in detail in copending applications Ser. Nos. 88,881 and 88,882, filed Oct. 29, 1979 in the name of Ralf Korpman which are incorporated by reference.

The bag may be prepared by cutting the film to any suitable shape and sealing the edges except for that part which is to be the opening. Thus, a bag having the shape of a flask with a neck, such as seen in FIGS. 1-6, is most conveniently prepared by cutting films to an appropriate shape and sealing the edges except at the top of the neck. A bag which has an opening near one end of a flat rectangular surface is most conveniently prepared by sealing the edges of two rectangular sheets, one of which has been slitted to provide an opening. Such a bag would be similar in FIGS. 7-8 except that the bottom of the bag would show a seal instead of a fold. The sealing may be carried out by heat, ultrasonic energy, adhesives, etc. The invention does not reside in the shape of the bag or in the method of its preparation; thus it may be adapted to any shape and to any known method of preparation.

I claim:

1. A self-sealing bag suitable for receiving body fluids and waste discharged from a surgically created orifice comprising a flexible, fluid-impervious receptacle provided with an opening, said bag made of a normally non-tacky, non-elastic film prepared from a composition consisting essentially of a blend of (a) a thermoplastic-elastomeric block copolymer component wherein the thermoplastic blocks are derived from alkenylarenes, possess a number average molecular weight of at least about 5,000, and constitute about 5 to 50 percent by weight of the block copolymer, and the elastomeric blocks are derived from conjugated dienes or lower alkenes, and possess a number average molecular weight of at least about 45,000, and (b) a resin component wherein the resin is one tending to associate with the thermoplastic alkenylarene blocks of the thermoplastic-elastomeric block copolymers and is employed in an amount of from about 30 to 130 parts per 100 parts by weight of the block copolymer, said film characterized by having the property of deforming on the application of a stretching force and changing from a non-tacky, plastic, inelastic material to a tacky, elastic material; and said film providing a sealing means to the opening of the bag when stretched at least 100 percent in the vicinity of the opening in a direction perpendicular to the opening, then relaxed and the sides of the opening pressed together.

2. A bag according to claim 1 in which the thermoplastic-elastomeric block copolymer component of the film is selected from the group consisting of polystyrene-polyisoprene-polystyrene and polystyrene-polybutadiene-polystyrene, and the resin component is selected from the group consisting of α-methylstyrene-vinyltoluene copolymer and coumarone-indene copolymer.

3. A bag according to claim 1 which bears an absorbent material, said absorbent material being a water-insoluble water-swellable lightly cross-linked organic polymer having a molecular weight per cross-linkage in the range of from about 13,000 to about 276,000.

4. A self-sealing surgical drainage bag comprising (1) a flexible, fluid impervious receptacle, said receptacle made of a normally non-tacky, non-elastic film prepared from a composition consisting essentially of a blend of (a) a thermoplastic-elastomeric block copolymer component wherein the thermoplastic blocks are derived from alkenylarenes, possess a number average molecular weight of at least about 5,000, and constitute about 5 to 50 percent by weight of the block copolymer, and the elastomeric blocks are derived from conjugated dienes or lower alkenes, possess a number average molecular weight of at least about 45,000; and (b) a resin component wherein the resin is one tending to associate with the thermoplastic alkenylarene blocks of the thermoplastic-elastomeric block copolymer, and the resin is employed in an amount of from about 30 to 130 parts per 100 parts by weight of the block copolymer, said film characterized by having the property of deforming on the application of a stretching force and changing from a non-tacky, plastic, inelastic material to a tacky, elastic material; and (2) a flexible non-disintegrative absorbent product comprising a water-insoluble substantially non-swelling matrix of an elastomeric or a thermoplastic material bearing uniformly dispersed particulate water-insoluble water-swellable organic polymer absorbent, said polymer absorbent being a lightly cross-linked polymer having a molecular weight per cross-linkage in the range of from about 13,000 to about 276,000.

5. A bag according to claim 4 in which the absorbent product constitutes a lining of the bag.

6. A process for removing body fluids and waste discharged from surgically created orifice which comprises receiving said fluid through an opening in a flexible, fluid impervious receptacle, said receptacle made of a normally non-tacky, non-elastic film prepared from a composition consisting essentially of a blend of (a) a thermoplastic-elastomeric block copolymer component wherein the thermoplastic blocks are derived from alkenylarenes, possess a number average molecular weight of at least about 5,000, and constitute about 5 to 50 percent by weight of the block copolymer, and the elastomeric blocks are derived from conjugated dienes or lower alkenes, possess a number average molecular weight of at least about 45,000; and (b) a resin component wherein the resin is one tending to associate with the thermoplastic alkenylarene blocks of the thermoplastic-elastomeric block copolymer, and the resin is employed in an amount of from about 30 to 130 parts per 100 parts by weight of the block copolymer; and said film characterized by having the property of deforming on the application of stretching force and changing from a non-tacky, plastic, inelastic material to a tacky elastic material; and said receptacle containing a flexible non-disintegrative absorbent product comprising a water-insoluble substantially non-swelling matrix of an elastomeric or a thermoplastic material bearing uniformly dispersed particulate water-insoluble water-swellable organic absorbent polymer having a molecular weight per cross-linkage in the range of from about 13,000 to about 276,000.

* * * * *